United States Patent
Koyama et al.

(10) Patent No.: US 11,016,283 B2
(45) Date of Patent: May 25, 2021

(54) OBJECTIVE OPTICAL SYSTEM, IMAGE PICKUP APPARATUS, AND ENDOSCOPE

(71) Applicant: OLYMPUS CORPORATION, Hachioji (JP)

(72) Inventors: Yutaka Koyama, Kawagoe (JP); Akari Morita, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/886,858

(22) Filed: May 29, 2020

(65) Prior Publication Data
US 2020/0292804 A1    Sep. 17, 2020

Related U.S. Application Data

(63) Continuation of application No. PCT/JP2018/032383, filed on Aug. 31, 2018.

(30) Foreign Application Priority Data

Jan. 26, 2018 (JP) .............. JP2018-011966

(51) Int. Cl.
*G02B 23/24* (2006.01)
*A61B 1/05* (2006.01)
*G02B 9/34* (2006.01)

(52) U.S. Cl.
CPC ............ *G02B 23/2484* (2013.01); *A61B 1/05* (2013.01); *G02B 9/34* (2013.01); *G02B 23/243* (2013.01)

(58) Field of Classification Search
USPC .......................................................... 348/65
See application file for complete search history.

(56) References Cited

U.S. PATENT DOCUMENTS

| 5,530,591 A | 6/1996 | Tachihara et al. |
| 5,724,190 A | 3/1998 | Tachihara et al. |
| 7,502,182 B2 | 3/2009 | Miyano |
| 7,907,352 B2 | 3/2011 | Miyano |
| 8,243,129 B2 | 8/2012 | Uzawa |

(Continued)

FOREIGN PATENT DOCUMENTS

| JP | H0792385 A | 4/1995 |
| JP | H07174966 A | 7/1995 |

(Continued)

OTHER PUBLICATIONS

International Search Report (ISR) (and English language translation thereof) dated Dec. 4, 2018 issued in International Application No. PCT/JP2018/032383.

(Continued)

*Primary Examiner* — Behrooz M Senfi
(74) *Attorney, Agent, or Firm* — Holtz, Holtz & Volek PC

(57) ABSTRACT

An objective optical system includes, in order from an object side to an image side, a front group having a negative refractive power, an aperture stop, and a rear group having a positive refractive power. The front group includes a negative single lens, the rear group includes, in order from the object side, a positive single lens and one or more cemented lenses, and following conditional expressions (1), (2), (3), and (5) are satisfied. $1.95 < ndCLn$ (1), $35 < \Delta vdCL$ (2), $1.1 < fL2/ft < 1.6$ (3), $-7 < R1/ft < -3.6$ (5).

20 Claims, 7 Drawing Sheets

(56) References Cited

U.S. PATENT DOCUMENTS

| | | | |
|---|---|---|---|
| 8,300,325 B2 | 10/2012 | Katahira | |
| 9,063,340 B2 | 6/2015 | Harada et al. | |
| 9,442,283 B2 | 9/2016 | Harada | |
| 9,618,731 B2 | 4/2017 | Ikegaya | |
| 9,622,652 B2* | 4/2017 | Igarashi | A61B 1/055 |
| 9,638,917 B2* | 5/2017 | Kawamura | G02B 15/20 |
| 9,696,526 B2 | 7/2017 | Inoue | |
| 9,709,796 B2 | 7/2017 | Harada et al. | |
| 9,804,380 B2 | 10/2017 | Igarashi | |
| 9,804,381 B2 | 10/2017 | Sato | |
| 10,007,105 B2 | 6/2018 | Kamo | |
| 10,016,119 B2* | 7/2018 | Watanabe | A61B 90/20 |
| 10,082,642 B2 | 9/2018 | Inoue | |
| 10,251,537 B2* | 4/2019 | Sato | A61B 1/04 |
| 10,459,214 B2 | 10/2019 | Inoue | |
| 2007/0188892 A1 | 8/2007 | Miyano | |
| 2008/0249367 A1 | 10/2008 | Miyano | |
| 2012/0007972 A1 | 1/2012 | Uzawa | |
| 2012/0127598 A1* | 5/2012 | Katahira | G02B 15/177 359/770 |
| 2014/0233113 A1 | 8/2014 | Harada et al. | |
| 2015/0131171 A1 | 5/2015 | Harada | |
| 2016/0299317 A1 | 10/2016 | Ikegaya | |
| 2016/0306161 A1 | 10/2016 | Harada et al. | |
| 2017/0023778 A1 | 1/2017 | Inoue | |
| 2017/0023779 A1* | 1/2017 | Inoue | G02B 27/0025 |
| 2017/0235121 A1 | 8/2017 | Igarashi | |
| 2017/0235122 A1 | 8/2017 | Sato | |
| 2017/0235123 A1 | 8/2017 | Kamo | |
| 2017/0285322 A1 | 10/2017 | Inoue | |
| 2019/0025568 A1 | 1/2019 | Matsuura | |

FOREIGN PATENT DOCUMENTS

| | | | |
|---|---|---|---|
| JP | 2004258611 A | 9/2004 |
| JP | 2007334291 A | 12/2007 |
| JP | 2008257108 A | 10/2008 |
| JP | 2011034106 A | 2/2011 |
| JP | 2016200743 A | 12/2016 |
| JP | 2016206336 A | 12/2016 |
| JP | 2017026801 A | 2/2017 |
| JP | 2017026802 A | 2/2017 |
| JP | 2017187563 A | 10/2017 |
| WO | 2011070897 A1 | 6/2011 |
| WO | 2011125539 A1 | 10/2011 |
| WO | 2013065296 A1 | 5/2013 |
| WO | 2014017031 A1 | 1/2014 |
| WO | 2016171043 A1 | 10/2016 |
| WO | 2016190184 A1 | 12/2016 |
| WO | 2016204000 A1 | 12/2016 |
| WO | 2017179373 A1 | 10/2017 |

OTHER PUBLICATIONS

Written Opinion dated Dec. 4, 2018 issued in International Application No. PCT/JP2018/032383.

Japanese Office Action (and English language translation thereof) dated Jan. 20, 2021 issued in Japanese Application No. 2019-567836.

International Preliminary Report on Patentability (IPRP) (and English language translation thereof) dated Aug. 6, 2020 issued in International Application No. PCT/JP2018/032383.

* cited by examiner

OBJECTIVE OPTICAL SYSTEM, IMAGE PICKUP APPARATUS, AND ENDOSCOPE

CROSS-REFERENCE TO RELATED APPLICATION

The present application is a continuation application of PCT/JP2018/032383 filed on Aug. 31, 2018 which is based upon and claims the benefit of priority from the prior Japanese Patent Application No. 2018-011966 filed on Jan. 26, 2018; the entire contents of which are incorporated herein by reference.

BACKGROUND

Technical Field

The disclosure relates to an objective optical system, mainly an objective optical system for a medical endoscope, an image pickup apparatus, and an endoscope.

Description of the Related Art

In recent years, with increase in pixels of image sensors, the size of a pixel decreases. For this reason, it is required to reduce various aberrations generated in objective optical systems of endoscopes. In particular, objective optical systems favorably correcting chromatic aberration of magnification, on axis chromatic aberration, and curvature of field are required. By contrast, endoscopes are used for observation in narrow body cavities. For this reason, it is required that the size of the optical system is small. The size of optical systems depends on the diameter of the lens and the total length of the lens. In addition, further miniaturization is required for objective optical systems for endoscopes used for observation of organs, such as the digestive organs, the bronchi, the nasal cavity, the pharyngolarynx, the urinary organs, and the uterus.

Japanese Unexamined Patent Application Publication No. 7-174966 discloses an objective optical system for an endoscope suppressing chromatic aberration of magnification by reducing the difference of the partial dispersion ratio.

Japanese Unexamined Patent Application Publication No. 7-92385 discloses an objective optical system for an endoscope using a low dispersion glass as at least one positive lens.

Japanese Unexamined Patent Application Publication No. 2004-258611 discloses a structure of removing a parallel plate, a structure of using a low dispersion glass for a positive lens of a cemented lens, and a structure of using a high dispersion glass for a positive lens.

Japanese Unexamined Patent Application Publication No. 2007-334291 discloses an objective optical system for an endoscope using a high dispersion glass for a negative lens of a cemented lens.

Japanese Unexamined Patent Application Publication No. 2016-206336 discloses an objective optical system for an endoscope providing relation between dispersion of a first negative lens and the refractive index.

SUMMARY

An objective optical system according to at least some embodiments includes:
in order from an object side to an image side, a front group having a negative refractive power;
an aperture stop; and
a rear group having a positive refractive power,
wherein
the front group includes a negative single lens,
the rear group includes, in order from the object side, a positive single lens and one or more cemented lenses, and
following conditional expressions (1), (2), (3), and (5) are satisfied:

$$1.95 < ndCLn \qquad (1)$$

$$35 < \Delta vdCL \qquad (2)$$

$$1.1 < fL2/ft < 1.6 \qquad (3)$$

$$-7 < R1/ft < -3.6 \qquad (5)$$

where
ndCLn denotes a refractive index of d line (wavelength of 587.6 nm) of a negative lens in the cemented lens,
$\Delta vdCL$ denotes a difference between an Abbe number of a positive lens and an Abbe number of the negative lens in the cemented lens,
ft denotes a focal length of an entire system of the objective optical system,
fL2 denotes a focal length of the positive single lens of the rear group, and
R1 denotes a curvature radius of an object side surface of the positive single lens.

In addition, an image pickup apparatus according to at least some embodiments includes:
an objective optical system which is described above.

In addition, an endoscope according to at least some embodiments includes:
an objective optical system which is described above.

BRIEF DESCRIPTION OF THE DRAWINGS

FIG. 2B, FIG. 2C, FIG. 2D, and FIG. 2E are aberration diagrams illustrating spherical aberration (SA), astigmatism (AS), distortion (DT), and chromatic aberration of magnification (CC) of the present example, respectively;

FIG. 3B, FIG. 3C, FIG. 3D, and FIG. 3E are aberration diagrams illustrating spherical aberration (SA), astigmatism (AS), distortion (DT), and chromatic aberration of magnification (CC) of the present example, respectively;

FIG. 5B, FIG. 5C, FIG. 5D, and FIG. 5E are aberration diagrams illustrating spherical aberration (SA), astigmatism (AS), distortion (DT), and chromatic aberration of magnification (CC) of the present example, respectively;

FIG. 6B, FIG. 6C, FIG. 6D, and FIG. 6E are aberration diagrams illustrating spherical aberration (SA), astigmatism (AS), distortion (DT), and chromatic aberration of magnification (CC) of the present example, respectively.

DETAILED DESCRIPTION

An objective optical system according to embodiments, for example, an objective optical system for an endoscope, will be described hereinafter in detail with reference to drawings.

The reason why such a structure is adopted for an objective optical system for an endoscope according to a first embodiment and functions thereof will now be described with reference to drawings. The present disclosure is not limited by the objective optical system for an endoscope according to the following embodiment.

The basic structure of the objective optical system for an endoscope according to the first embodiment will now be described. The objective optical system for an endoscope having the basic structure includes, in order from an object side, a front group having a negative refractive power, an aperture stop, and a rear group having a positive refractive power. The front group includes a negative single lens. The rear group includes, in order from the object side, a positive single lens and one or more cemented lenses.

An objective optical system for an endoscope according to the present embodiment requires a length of a back focus, to acquire a wide angle of view and to achieve easy adjustment in an assembly process. For this reason, a structure of what is called a retrofocus type is adopted as the basic structure.

Figure 1A:
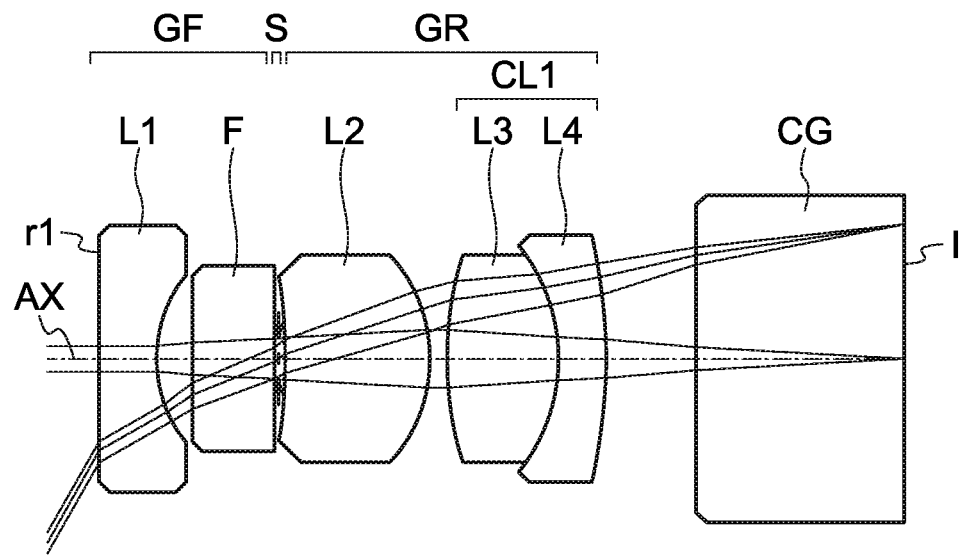
FIG. 1A is a lens cross-sectional view of an objective optical system for an endoscope according to a first embodiment.

FIG. 1A is a lens cross-sectional view illustrating an example of the basic structure of the objective optical system for an endoscope according to the present embodiment. In the basic structure, the optical system is formed of, in order from the object side, a front group GF having a negative refractive power, an aperture stop S, and a rear group GR having a positive refractive power.

In addition, in the basic structure, the rear group GR includes a cemented lens CL1 formed of a positive lens L3 and a negative lens L4. In this manner, chromatic aberration is corrected.

In addition, the rear group GR includes a positive single lens L2 (first positive single lens L2). To secure a wide angle of view, it is required to provide the front group GF with a large negative refractive power. To achieve a positive refractive power in the entire system of the optical system, it is required to dispose a large positive refractive power in the rear group GR. This is secured with the positive single lens L2 of the rear group GR. In addition, when the positive single lens L2 is disposed on the rear side (image surface side), with one or more lenses interposed therebetween, not directly after the aperture stop S, the position which the off axis light beam passes through becomes distant from an optical axis AX. For this reason, this is not desirable because the effective diameter of the lens increases. Accordingly, the structure as in the present embodiment is adopted. In the structure, the positive single lens L2 disposed in the rear of the aperture stop S is a single lens and has a positive refractive power.

As described above, the basic structure in the objective optical system for an endoscope according to the present embodiment is a structure suitable for reduction in diameter, that is, reduction in diameter of the lens outer diameter, shortening of the total length of the optical system, and correction of chromatic aberration and the like.

The front group GF is formed of a negative single lens L1 (first negative single lens L1) and an optical filter F. The rear group GR is formed of the positive single lens L2 and the cemented lens CL1. The cemented lens CL1 is formed of the positive lens L3 and the negative lens L4.

The aperture stop S is disposed between the front group GF and the rear group GR. The aperture stop S may be provided on a lens surface. As a method for providing the aperture stop S on a lens surface, for example, there are a method of coating the lens surface with a metal light-shielding film and forming an opening by etching, and a method of inserting an annular thin metal plate between the lens and the frame.

In FIG. 1A, the optical filter F is disposed between the negative single lens L1 and the aperture stop S.

The optical filter F is, for example, an infrared ray cut filter, or a color temperature conversion filter. The optical filter F of these types is used for correction of sensitivity of the image sensor, such as a CCD.

A laser cut filter and/or a special function filter may be disposed in the optical system. The laser cut filter is, for example, a filter to cut laser light, such as YAG laser and semiconductor laser. The special function filter is, for example, a notch filter to cut light beam of a specific wavelength region.

As another example, an absorption type filter, a reflection type filter, or a complex type filter combining them may be used as the optical filter F. As another example, a filter provided with an antireflection film may be used.

The rear group GR is formed of the positive single lens L2 and the cemented lens CL1. The cemented lens CL1 is formed of the positive lens L3 and the negative lens L4.

A lens surface on an object side of the positive single lens L2 of the rear group GR has a concave shape. A lens surface on an image side of the positive single lens L2 has a convex shape. As described above, the positive single lens L2 is a meniscus lens.

A glass block CG is disposed on the image side of the rear group GR. The glass block CG is supposed to be a cover glass of a solid state image sensor. An image of an object having an image height of IH is formed on an image pickup surface I in an image side surface of the glass block CG. The image side surface of the glass block CG agrees with the image pickup surface I of the image sensor.

The objective optical system for an endoscope according to the first embodiment will be further explained hereinafter.

The objective optical system for an endoscope according to the first embodiment has the basic structure described above, and satisfies the following conditional expressions (1), (2), and (3) are satisfied:

$$1.95 < ndCLn \tag{1}$$

$$35 < \Delta vdCL \tag{2}$$

$$1.1 < fL2/ft < 1.6 \tag{3}$$

where ndCLn denotes a refractive index of d line (wavelength of 587.6 nm) of the negative lens L4 in the cemented lens CL1 of the rear group GR, ΔvdCL denotes a difference between an Abbe number of the positive lens L3 and an Abbe number of the negative lens L4 in the cemented lens CL1 of the rear group GR, ft denotes a focal length of an entire system of the objective optical system for the endoscope, and fL2 denotes a focal length of the positive single lens L2 of the rear group GR.

The conditional expression (1) provides a condition to favorably correct the curvature of field. A high refractive index glass material is used for the negative lens L4 of the cemented lens CL1. In this manner, the absolute value of the total value (Petzval sum) of values obtained by dividing the refractive power of each of the lenses by the refractive index of the glass material is reduced.

When the value of the conditional expression (1) is smaller than the lower limit value, the absolute value of the Petzval sum is large, that is, the curvature of field increases, and it is impossible to acquire a favorable observation image in the entire field of view.

In an objective optical system for an endoscope having a wide angle of view, Petzval sum is negative in many cases. For this reason, to decrease the Petzval sum, it is required to use a high refractive index glass material for the negative lens, or use a low refractive index glass material for the positive lens. However, when a low refractive index glass material is used for the positive lens, spherical aberration and/or coma occurs, and the image quality deteriorates. For this reason, it is more desirable to use a high refractive index glass material for the negative lens.

In the present embodiment, it is possible to use a high refractive index glass material for the negative single lens L1 of the front group GF. However, alternatives of the glass material that can be used for the negative single lens L1 exposed at a distal end portion of the endoscope are limited from the viewpoint of biocompatibility. For this reason, a high refractive index glass material is used for the negative lens L4 of the cemented lens CL1 of the rear group GR.

The conditional expression (2) is a conditional expression to favorably correct chromatic aberration of magnification. In the present embodiment, chromatic aberration is corrected with the cemented lens CL1 of the rear group GF. Regarding the difference in Abbe number between the positive lens L3 and the negative lens L4, the difference in Abbe number of the conditional expression (2) is smaller than the lower limit value, correction of the chromatic aberration of magnification is insufficient, and the image quality deteriorates in the periphery of the field of view.

The conditional expression (3) is a conditional expression to shorten the total lens length of the objective optical system for an endoscope and relating to the positive single lens L2 of the rear group GR. When the value is larger than the upper limit value of the conditional expression (3), the refractive power of the positive single lens L2 decreases. For this reason, the whole lens length increases, and miniaturization of the lens becomes difficult.

When the value of the conditional expression (3) is smaller than the lower limit value, the positive refractive power becomes too large. This is not desirable because spherical aberration and/or off axis coma increases.

In addition, in the objective optical system for an endoscope according to the first embodiment, it is preferable that the positive single lens L2 included in the rear group GR satisfies the following expression (4).

$$1.75 < ndL2 \quad (4)$$

wherein ndL2 denotes a refractive index of d line of the positive single lens L2 of the rear group GR.

When the value of the conditional expression (4) is smaller than the lower limit value, the curvature radius of the image side surface of the positive single lens L2 of the rear group GR becomes too small, the off axis chief ray is greatly curved, and off axis coma increases.

In addition, in the objective optical system for an endoscope according to the first embodiment, it is preferable that the positive single lens L2 in the rear group GR satisfies the following conditional expressions (5) and (6):

$$-7 < R1/ft < -3.6 \quad (5)$$

$$0.8 < |R2/Ls2| < 1.2 \quad (6)$$

where

R1 denotes a curvature radius of an object side surface of the positive single lens L2 in the rear group GR, ft denotes a focal length of an entire system of the objective optical system for the endoscope, R2 denotes a curvature radius of an image side surface of the positive single lens L2 in the rear group GR, and Ls2 denotes a distance along the optical axis AX from the aperture stop S to the image side surface of the positive single lens L2.

When the value of the conditional expression (5) is larger than the upper limit value, the refractive power of the positive single lens L2 of the rear group GR decreases. It is possible to equalize the focal length and the angle of view of the entire objective optical system by increasing the positive refractive power of the cemented lens CL1, but also in this case this is not preferable because the whole lens length increases.

Also when the value is smaller than the lower limit value of the conditional expression (5), the whole lens length increases. This is because the position (apex) of an intersection point of the image side surface and the optical axis becomes close to the image with respect to the position of the principal point of the positive single lens L2 of the rear group GR, and a restriction of disposing the subsequent lens more on the image side occurs.

When the positions of the principal points are aligned, it is known that the apex on the image side of a plano-convex lens is disposed closer to the object side, and the apex on the image side of a meniscus lens having a concave surface on the object side is disposed further closer to the object side, in comparison with a biconvex lens. For this reason, by using a meniscus lens satisfying such a condition, it is possible to increase the degree of freedom of lens arrangement on the image side after the meniscus lens. More specifically, it is possible to dispose other optical elements close to the positive single lens L2.

The conditional expression (6) is a conditional expression to suppress occurrence of off axis coma in the object side surface of the positive single lens L2 of the rear group GR. When the value of the conditional expression (6) is larger than the upper limit value, the coma markedly occurs, and the image quality around the field of view deteriorates. By contrast, also when the value of the conditional expression (6) is smaller than the lower limit value, this is not preferable because coma of the opposite sign occurs.

In addition, in the objective optical system for an endoscope according to the first embodiment, it is preferable that the front group GF includes a parallel plate F, and the following conditional expression (7) is satisfied:

$$1.4 < Lgr/Lgf < 2 \tag{7}$$

where

Lgf denotes a distance along the optical axis AX from the object side surface of the negative single lens L1 of the front group GF to the aperture stop S, and Lgr denotes a distance along the optical axis AX from the aperture stop S to a surface located most on the image side in the lenses of the rear group GR.

When the value of the conditional expression (7) is larger than the upper limit value, the light beam height increases in the cemented lens CL1 of the rear group GR. For this reason, the lens diameter increases, and miniaturization of the objective optical system becomes difficult.

When the value is smaller than the lower limit value of the conditional expression (7), conversely the light beam height increases at the object side surface of the negative single lens L1 of the front group GF. This is not preferable because the lens diameter of the negative single lens L1 and miniaturization of the objective optical system for an endoscope becomes difficult.

In addition, in the objective optical system for an endoscope according to the present embodiment, it is preferable that the negative single lens L1 of the front group GF is a plano-concave lens, an object side surface thereof is a flat surface, and a concave surface thereof is opposed to the image side.

In addition, in the objective optical system for an endoscope according to the present embodiment, it is preferable that the negative single lens L1 of the front group GF is a plano-concave lens including a flat surface disposed as the object side surface and the following conditional expression (9) is satisfied:

$$0.5 < D1/R1L1 < 0.9 \tag{9}$$

where

R1L1 denotes a curvature radius of the image side surface of the negative single lens L1 of the front group GF, and D1 is a radius of a spherical (concave) segment of the image side surface of the negative single lens L1 in the front group GF, in a direction perpendicular to the optical axis AX.

When the value of the conditional expression (9) is larger than the upper limit value, miniaturization of the objective optical system for an endoscope becomes difficult. When the value of D1 is large, the lens diameter of the negative single lens L1 increases. By contrast, when the value of R1L1 decreases, the spherical segment becomes deeper when the effective diameter through which the light beam passes is secured. In this manner, the total thickness of the negative single lens L1 from the object side surface to the image side surface increases, and shortening of the whole lens length becomes difficult.

Also when the value of the conditional expression (9) is smaller than the lower limit value, the lens diameter increases. This is because the peripheral light beam height passing through either the object side surface or the image side surface increases due to reduction of the negative refractive power by increase in the value of R1L1, and the lens diameter increases. To achieve good image quality required for the objective optical system for an endoscope, it is required to avoid diffraction blurring. To achieve it, it is impossible to greatly reduce the luminous flux diameter (this determines D1) passing through the image side surface.

In the objective optical system for an endoscope according to the present embodiment, it is preferable that the cemented lens CL1 includes, in order from the object side, the positive lens L3 and the negative lens L4, and the following conditional expression (10) is satisfied:

$$-2 < R1CL < ft < -1.1 \tag{10}$$

where

R1CL denotes a curvature radius of the cemented surface of the cemented lens CL1 of the rear group GR, and ft denotes a focal length of the entire system of the objective optical system for an endoscope.

When the value of the conditional expression (10) is larger than the upper limit value, the refractive power acting at the cemented surface becomes too strong. This is not preferable because the off axis coma increases. In addition, this is not preferable because processing of both the positive lens L3 and the negative lens L4 becomes difficult and the cost increases.

When the value of the conditional expression (10) is smaller than the lower limit value, the refractive power acting on the off axis light beam at the cemented surface is insufficient. This is not preferable because it is impossible to sufficiently correct chromatic aberration of magnification.

The reason why such a structure is adopted for an objective optical system for an endoscope according to a second embodiment and functions thereof will now be described with reference to drawings.

Figure 1B:
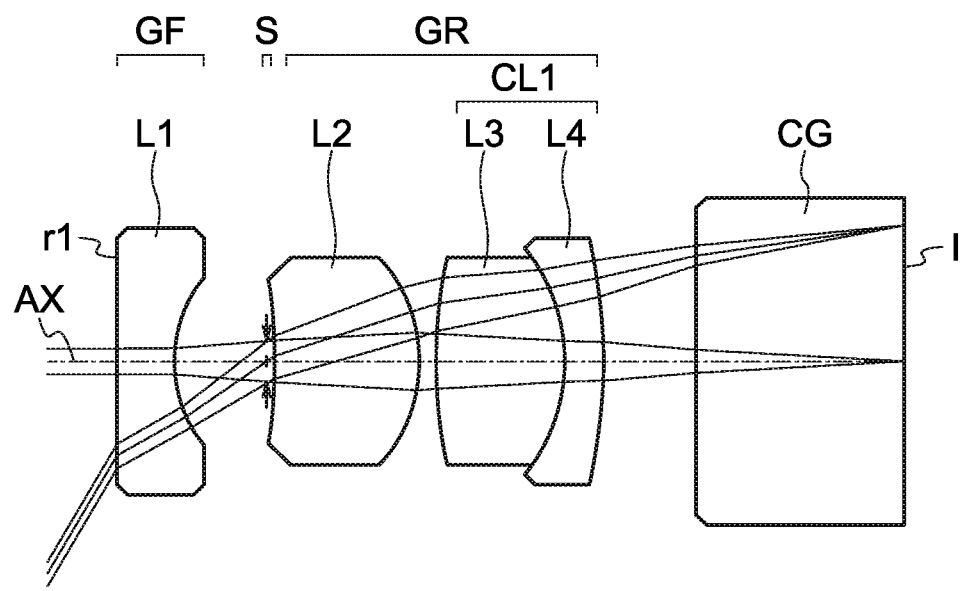
FIG. 1B is a lens cross-sectional view of an objective optical system for an endoscope according to a second embodiment.

FIG. 1B is a lens cross-sectional view illustrating an example of a basic structure of an objective optical system for an endoscope according to the present embodiment.

The objective optical system for an endoscope according to the second embodiment includes, in order from the object side, a front group GF having a negative refractive power, an aperture stop S, and a rear group GR having a positive refractive power.

The rear group GR includes a cemented lens CL1 formed of a positive lens L3 and a negative lens L4.

In the objective optical system for an endoscope according to the second embodiment, it is preferable that the front group GF includes only a negative single lens L1 and the following conditional expression (8) is satisfied:

$$1.9 < Lgr/ft < 2.6 \tag{8}$$

where

Lgr denotes a distance along an optical axis AX from the aperture stop S to a surface located most on the image side in the lenses of the rear group GR, and ft denotes a focal length of the entire system of the objective optical system for an endoscope.

When the value of the conditional expression (8) is larger than the upper limit value, the light beam height increases at the cemented lens CL1 of the rear group GR. For this reason, the lens diameter increases, and miniaturization of the objective optical system becomes difficult.

When the value of the conditional expression (8) is smaller than the lower limit value, it is impossible to sufficiently correct various aberrations, such as coma and chromatic aberration, with the rear group GR. This is not preferable because the image quality deteriorates.

In the objective optical system for an endoscope according to the second embodiment, the structures and the conditional expressions of the negative single lens L1 of the front group GF and the rear group GR are the same as the meanings of the structures and the conditional expressions in the objective optical system for an endoscope according to the first embodiment. For this reason, an overlapping explanation is omitted.

In addition, in the objective optical system for an endoscope according to the first embodiment and the objective optical system for an endoscope according to the second embodiment, it is preferable that the negative single lens L1 of the front group GF is a plano-concave lens including an object side surface being a flat surface.

By forming the object side surface as a flat surface, it is possible to reduce breakage of the lens surface. In addition, because water drops are prevented from accumulating in the peripheral portion of the lens surface, drainage is improved, and an observable range is not narrowed.

In addition, in the objective optical systems for endoscopes according to the first embodiment and the second embodiment, it is preferable that nd of the positive lens L3 of the cemented lens CL1 is 1.65 or less.

In addition, in the objective optical systems for endoscopes according to the first embodiment and the second embodiment, it is preferable that the Abbe number of the negative lens L4 of the cemented lens CL1 is 20 or less.

The objective optical systems for an endoscope described above may simultaneously satisfy a plurality of structure. This is preferable to acquire a favorable objective optical system for an endoscope. In addition, preferable structures may be combined as desired. For each of the conditional expressions, only the upper limit value or the lower limit value of the numerical range of a more limited conditional expression may be limited.

Examples will be explained hereinafter. The lens cross-sectional view in each of examples illustrates light beams made incident from the object side and passing through the center of the aperture stop S and both ends of the internal cross section of the aperture stop S. In each of aberration diagrams, the horizontal axis indicates an aberration quantity. With respect to spherical aberration and astigmatism, the unit of the aberration quantity is "mm". With respect to the distortion, the unit of the aberration quantity is "%". IH denotes the maximum image height with the unit of "mm", and FNO denotes an F number. The unit of the wavelength of the aberration curve is "nm".

Example 1

Figure 2A:
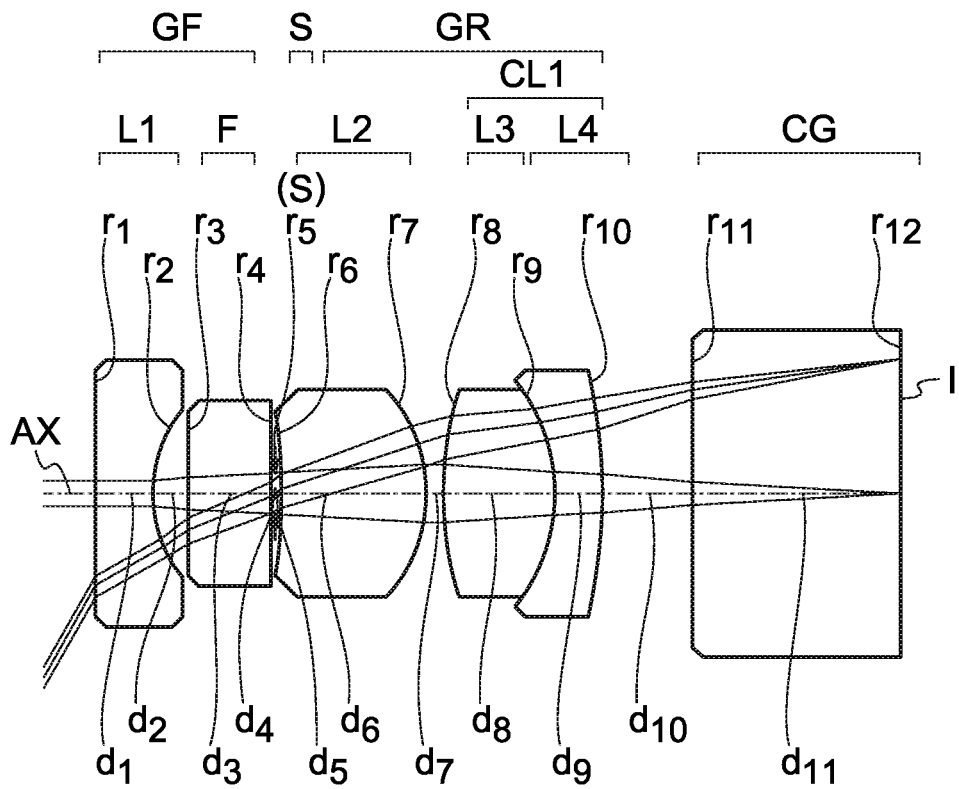
FIG. 2A is a lens cross-sectional view of an objective optical system for an endoscope according to Example 1.
Figure 2A:
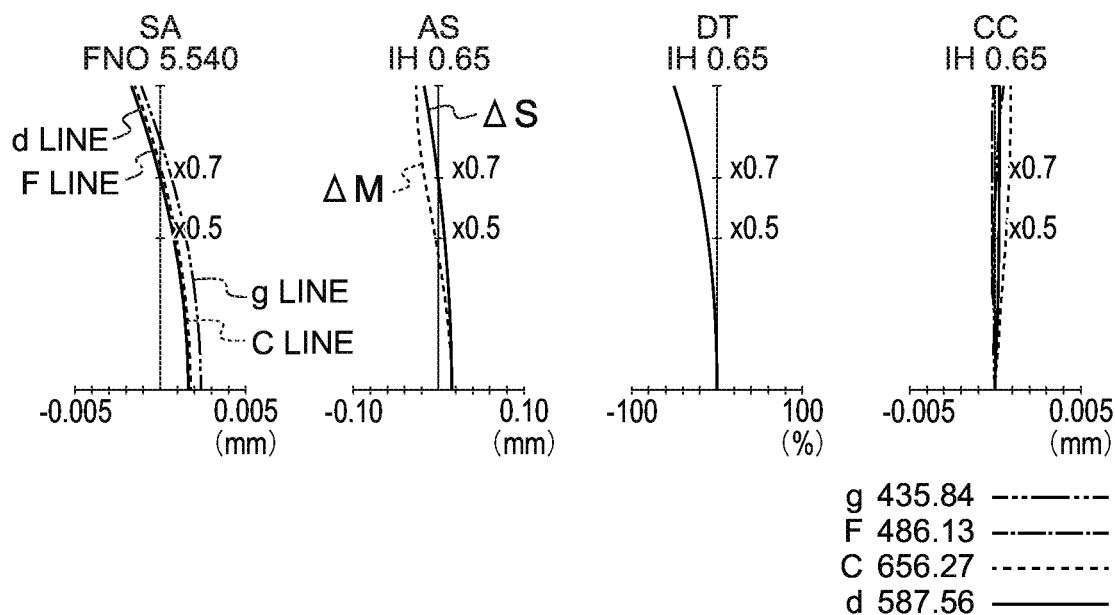

An objective optical system for an endoscope according to Example 1 will be explained hereinafter. FIG. 2A is a lens cross-sectional view of the objective optical system for an endoscope according to Example 1. FIG. 2B illustrates spherical aberration (SA), FIG. 2C illustrates astigmatism (AS), FIG. 2D illustrates distortion (DT), and FIG. 2E illustrates chromatic aberration of magnification (CC).

The objective optical system for an endoscope according to Example 1 includes, in order from the object side, a front group GF having a negative refractive power, an aperture stop S, and a rear group GR having a positive refractive power, as illustrated in FIG. 2A.

The front group GF is formed of a plano-concave negative first lens L1 including a flat surface on the object side, and an optical filter F.

The rear group GR is formed of a positive second meniscus lens L2 including a concave surface on the object side, a biconvex positive third lens L3, and a negative fourth meniscus lens L4 including a convex surface opposed to the image side. In this structure, the biconvex positive third lens L3 and the negative fourth meniscus lens L4 form a cemented lens CL1 having a positive refractive power.

The aperture stop S is provided on the image side surface of the optical filter F. The optical filter F is disposed in the front group GF. The optical filter F is disposed between the plano-concave negative first lens L1 and the aperture stop S. On the image side of the rear group GR, a glass block CG is disposed, on the assumption that a cover glass of a solid state image sensor is disposed.

A space between the cemented lens CL1 and the glass block CG serves as a focus adjustment interval, to achieve optical design to sufficiently secure the adjustment width.

The characteristics of the negative first lens L1 will be described later. In the negative first lens L1, the object side surface is a flat surface. This structure is ordinary as an endoscope distal end structure. In an endoscope, because illumination light is made incident directly when the object side surface is formed as a convex surface, it is required to devise a light-shielding structure at the distal end portion of the endoscope. For this reason, Example 1 has the advantage that no device for light shielding is required in the negative first lens L1 or the frame structure against a direct light incident flare from the illumination system (not illustrated).

In addition, because the object side of the negative first lens L1 is a flat surface, no protrusion (convex shape) exists on the object side. For this reason, even any object collides with the lens surface from the object side, the probability that the negative first lens L1 is damaged is lower than that in the case where the object side thereof is a concave surface.

The glass material of the negative first lens L1 is preferably sapphire having excellent mechanical durability. By using sapphire, occurrence of reflection of scratches on the image and flares caused by scratches is suppressed. However, the glass material of the negative first lens L1 is not limited to sapphire.

The optical filter F is, for example, a color correction filter. The color correction filter is formed of an absorption material attenuating a wavelength from a long wavelength side of a visible range to a near infrared wavelength range. However, Nd/YAG laser may be used to treat a tumor or the like for use for gastroenterology, respiratory, urology, or otorhinolaryngology. For this reason, it is desirable to provide a multilayer optical interference film having reflectivity of substantially 100% with respect to the wavelength of Nd/YAG laser on one surface or both surfaces of the color correction filter.

The cemented lens CL1 is formed of the positive third lens L3 of a low refractive index glass material and the negative fourth meniscus lens L4 of a high refractive index glass material. In addition, by providing a negative refractive power to the cemented surface, astigmatism and coma are corrected. In addition, by setting a large difference between the refractive index on the object side and the refractive index on the image side of the cemented surface, consideration is made to prevent excessive reduction in the curvature radius of the cemented surface. In this manner, fluctuations in aberration due to eccentricity are suppressed. No lens capable of correcting chromatic aberration of magnification exists on the object side beyond the cemented lens CL1. For this reason, ultrahigh dispersion glass is used for the negative fourth meniscus lens L4 of the cemented lens CL1, and chromatic aberration of magnification is corrected all together in the cemented lens CL1.

Chromatic aberration of magnification of the objective optical system for an endoscope according to Example 1 will be described hereinafter. The maximum image height IH thereof is 0.652 mm. As illustrated in FIG. 2E, chromatic aberration of magnification is 1.5 μm or less, and this corresponds to 0.23% on the half of the diagonal. Generally, when the chromatic aberration of magnification is 3 pixels or less, the image quality is not influenced. Even when a full-HD (1920 pixels×1080 pixels) image sensor is used, the half of the diagonal is 1101 pixels, and 0.23% thereof is 2.5 pixels that are equal to or smaller than 3 pixels.

The total length of the objective optical system for an endoscope according to Example 1 will be described hereinafter. The distance from the first surface on the object side of the lens to the image surface is 5.38 times as long as the focal length, and shorter than the prior art documents. For this reason, it is suitable for an objective optical system for an endoscope with a small-sized distal end portion and high image quality.

Example 2

Figure 3A:
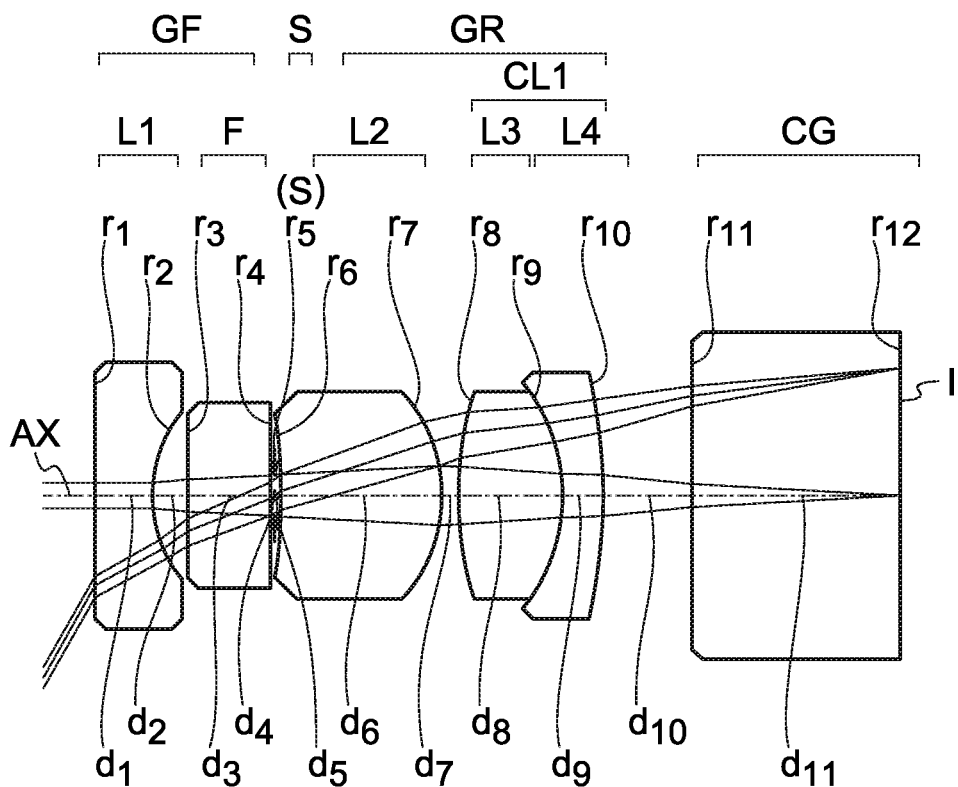
FIG. 3A is a lens cross-sectional view of an objective optical system for an endoscope according to Example 2.
Figure 3A:
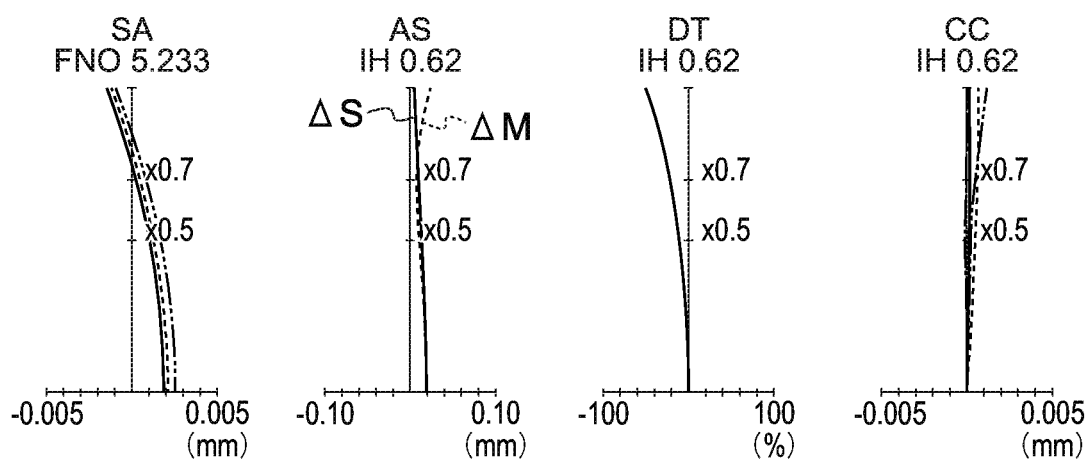

An objective optical system for an endoscope according to Example 2 will be described hereinafter. FIG. 3A is a lens cross-sectional view of the objective optical system for an endoscope according to Example 2. FIG. 3B illustrates spherical aberration (SA), FIG. 3C illustrates astigmatism (AS), FIG. 3D illustrates distortion (DT), and FIG. 3E illustrates chromatic aberration of magnification (CC).

The objective optical system for an endoscope according to Example 2 includes, in order from the object side, a front group GF having a negative refractive power, an aperture stop S, and a rear group GR having a positive refractive power, as illustrated in FIG. 3A.

In the objective optical system for an endoscope according to Example 2, a glass material of nd=1.816 is used for the positive second meniscus lens L2, and a glass material of nd=1.569 is used for the negative fourth meniscus lens L4 of the cemented lens CL1.

The lens structure in Example 2 is the same as the lens structure in Example 1, and an overlapping explanation is omitted.

The chromatic aberration of magnification of the objective optical system for an endoscope according to Example 2 will be described hereinafter. The maximum image height IH thereof is 0.615 mm. As illustrated in FIG. 3E, the chromatic aberration of magnification is 1.4 μm or less, and this corresponds to 0.23% of half side of the diagonal. In the same manner as the objective optical system for an endoscope according to Example 1, it is considered that the chromatic aberration of magnification causes no problem.

The total length of the objective optical system for an endoscope according to Example 2 will be described hereinafter. The distance from the first surface on the object side of the lens to the image surface is 5.7 times as long as the focal length, and shorter than the prior art documents. For this reason, it is suitable for an objective optical system used for an endoscope with a small-sized distal end portion and high image quality.

Example 3

Figure 4A:
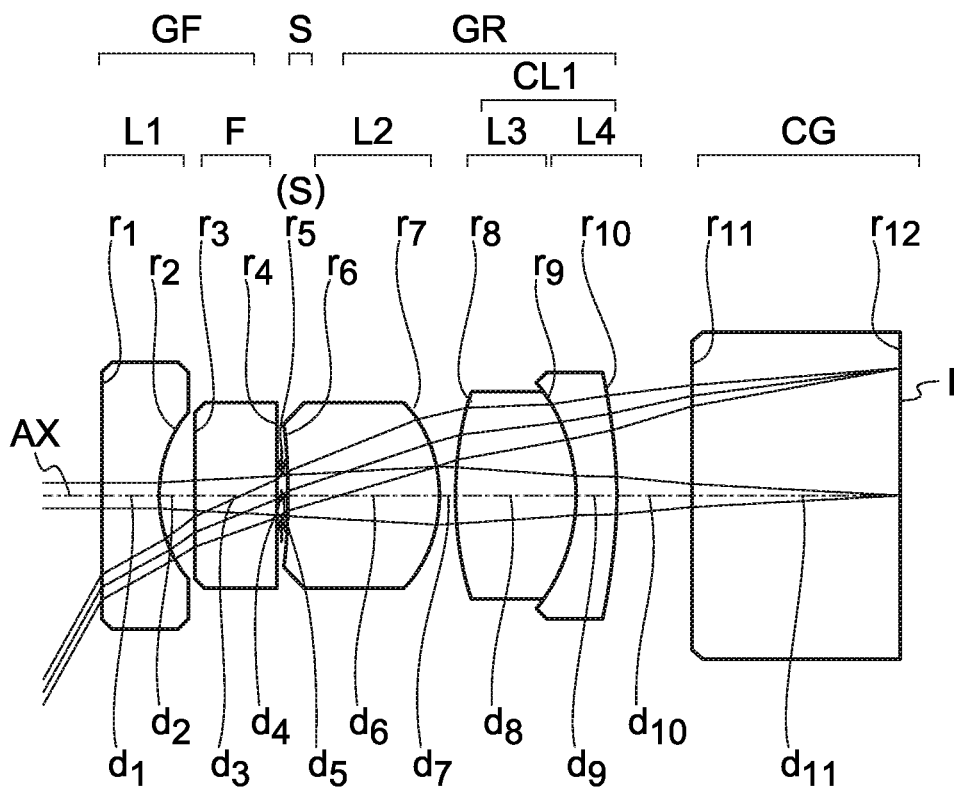
FIG. 4A is a lens cross-sectional view of an objective optical system for an endoscope according to Example 3.
Figures 4B, 4C, 4D, 4E:
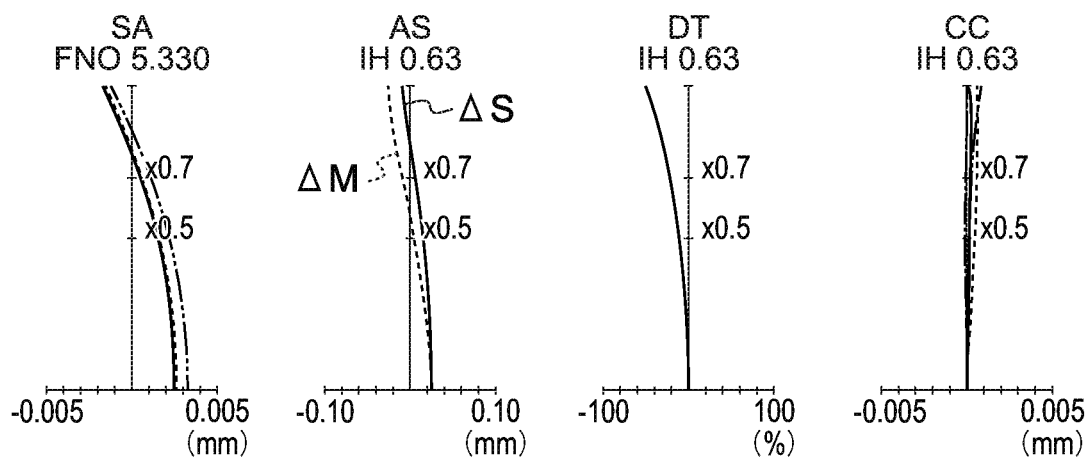
FIG. 4B, FIG. 4C, FIG. 4D, and FIG. 4E are aberration diagrams illustrating spherical aberration (SA), astigmatism (AS), distortion (DT), and chromatic aberration of magnification (CC) of the present example, respectively.

An objective optical system for an endoscope according to Example 3 will be described hereinafter. FIG. 4A is a lens cross-sectional view of the objective optical system for an endoscope according to Example 3. FIG. 4B illustrates spherical aberration (SA), FIG. 4C illustrates astigmatism (AS), FIG. 4D illustrates distortion (DT), and FIG. 4E illustrates chromatic aberration of magnification (CC).

The objective optical system for an endoscope according to Example 3 includes, in order from the object side, a front group GF having a negative refractive power, an aperture stop S, and a rear group GR having a positive refractive power, as illustrated in FIG. 4A.

In the objective optical system for an endoscope according to Example 3, a glass material of nd=1.772 is used for the positive second meniscus lens L2, and a glass material of nd=1.538 is used for the negative fourth meniscus lens L4 of the cemented lens CL1.

The lens structure in Example 3 is the same as the lens structure in Example 1, and an overlapping explanation is omitted.

The chromatic aberration of magnification of the objective optical system for an endoscope according to Example 3 will be described hereinafter. The maximum image height IH thereof is 0.625 mm. As illustrated in FIG. 4E, the chromatic aberration of magnification is 1.4 μm or less, and this corresponds to 0.23% of half side of the diagonal. In the same manner as the objective optical system for an endoscope according to Example 1, it is considered that the chromatic aberration of magnification causes no problem.

The total length of the objective optical system for an endoscope according to Example 3 will be described hereinafter. The distance from the first surface on the object side of the lens to the image surface is 5.54 times as long as the focal length, and shorter than the prior art documents. For this reason, it is suitable for an objective optical system used for an endoscope with a small-sized distal end portion and high image quality.

Example 4

Figure 5A:
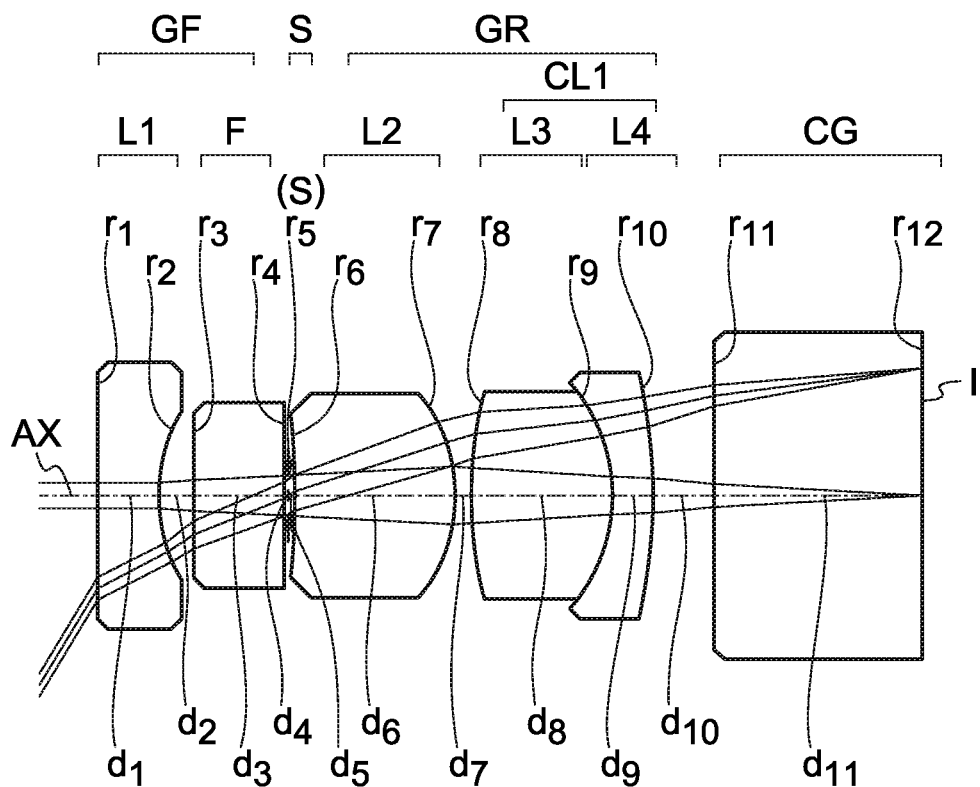
FIG. 5A is a lens cross-sectional view of an objective optical system for an endoscope according to Example 4.
Figure 5A:
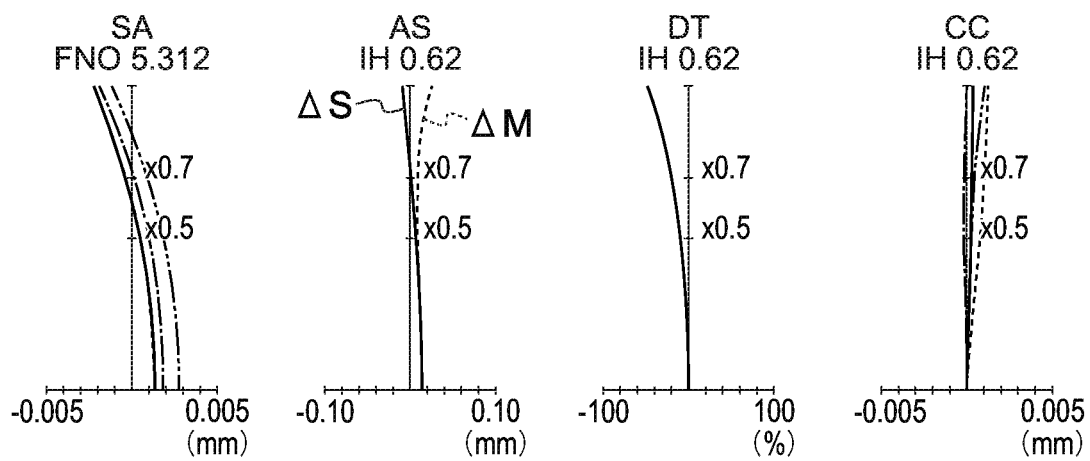

An objective optical system for an endoscope according to Example 4 will be described hereinafter. FIG. 5A is a lens cross-sectional view of the objective optical system for an endoscope according to Example 4. FIG. 5B illustrates spherical aberration (SA), FIG. 5C illustrates astigmatism (AS), FIG. 5D illustrates distortion (DT), and FIG. 5E illustrates chromatic aberration of magnification (CC).

The objective optical system for an endoscope according to Example 4 includes, in order from the object side, a front group GF having a negative refractive power, an aperture stop S, and a rear group GR having a positive refractive power, as illustrated in FIG. 5A.

In the objective optical system for an endoscope according to Example 4, a glass material of nd=1.883 is used for the negative first lens L1, a glass material of nd=1.816 is used for the positive second meniscus lens L2, and a glass material of nd=1.64 is used for the negative fourth meniscus lens L4 of the cemented lens CL1.

In Example 4, optical glass other than sapphire is used as the glass material of the negative first lens L1. Although mechanical durability of the optical glass is inferior to that of sapphire, workability of the optical glass is superior to that of sapphire. By virtue of advantage of the price and workability of the optical glass, it is possible to manufacture the lens at lower cost than that in the case of using sapphire.

The lens structure in Example 4 is the same as the lens structure in Example 1, and an overlapping explanation is omitted.

The chromatic aberration of magnification of the objective optical system for an endoscope according to Example 4 will be described hereinafter. The maximum image height IH thereof is 0.622 mm. As illustrated in FIG. 5E, the chromatic aberration of magnification is 1.6 μm or less, and this corresponds to 0.26% of half side of the diagonal. In the same manner as the objective optical system for an endoscope according to Example 1, it is considered that the chromatic aberration of magnification causes no problem.

The total length of the objective optical system for an endoscope according to Example 4 will be described hereinafter. The distance from the first surface on the object side of the lens to the image surface is 5.74 times as long as the focal length, and shorter than the prior art documents. For this reason, it is suitable for an objective optical system used for an endoscope with a small-sized distal end portion and high image quality.

Example 5

Figure 6A:
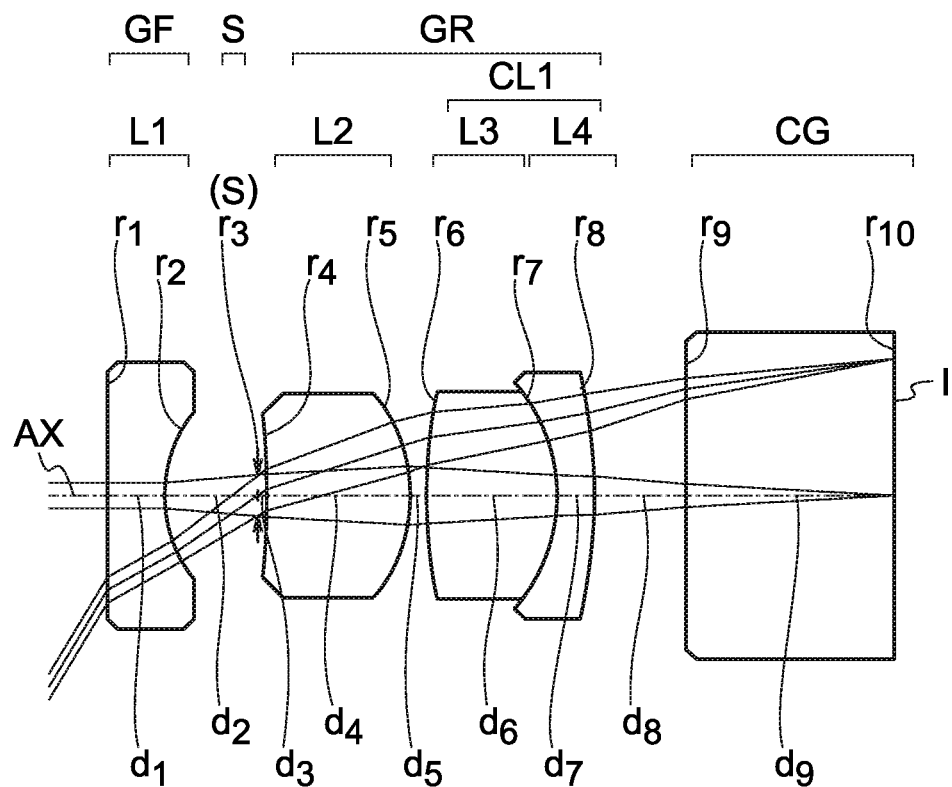
FIG. 6A is a lens cross-sectional view of an objective optical system for an endoscope according to Example 5.
Figure 6A:
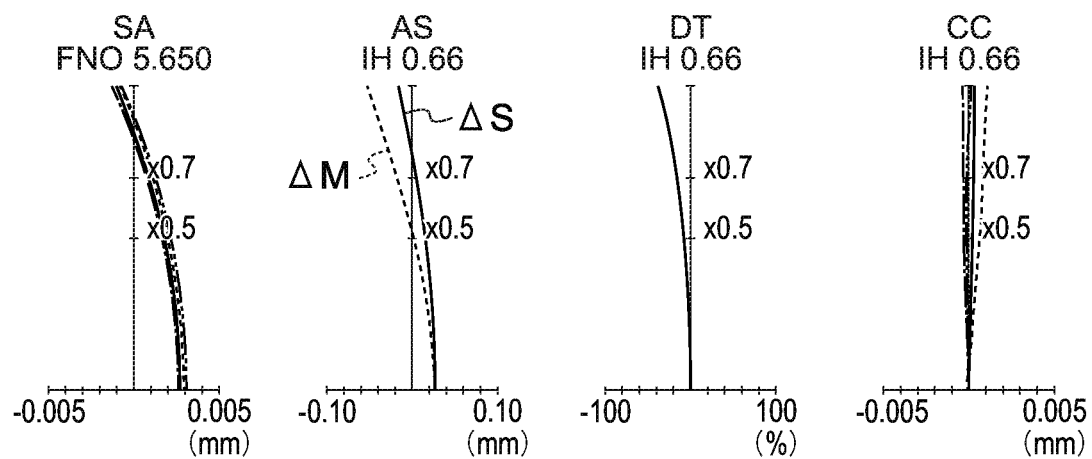

An objective optical system for an endoscope according to Example 5 will be described hereinafter. FIG. 6A is a lens cross-sectional view of the objective optical system for an endoscope according to Example 5. FIG. 6B illustrates spherical aberration (SA), FIG. 6C illustrates astigmatism (AS), FIG. 6D illustrates distortion (DT), and FIG. 6E illustrates chromatic aberration of magnification (CC).

The objective optical system for an endoscope according to Example 5 includes, in order from the object side, a front group GF having a negative refractive power, an aperture stop S, and a rear group GR having a positive refractive power, as illustrated in FIG. 6A.

The front group GF is formed of a plano-concave negative first lens L1 including a flat surface on the object side.

The rear group GR is formed of a positive second meniscus lens L2 including a concave surface on the object side, a biconvex positive third lens L3, and a negative fourth meniscus lens L4 including a convex surface opposed to the image side. In this structure, the biconvex positive third lens L3 and the negative fourth meniscus lens L4 form a cemented lens CL1 having a positive refractive power.

The aperture stop S is provided between the negative first lens L1 and the positive second meniscus lens L2. On the image side of the rear group GR, a glass block CG is disposed, on the assumption that a cover glass of a solid state image sensor is disposed.

A space between the cemented lens CL1 and the glass block CG serves as a focus adjustment interval, to achieve optical design to sufficiently secure the adjustment width.

In the objective optical system for an endoscope according to Example 5, a glass material of nd=1.816 is used for the positive second meniscus lens L2, and a glass material of nd=1.622 is used for the negative fourth meniscus lens L4 of the cemented lens CL1.

In Example 5, the structures and the conditional expressions of the negative single lens L1 of the front group GF and the rear group GR are the same as the structures and the conditional expressions in the objective optical system for an endoscope according to Example 1. For this reason, an overlapping explanation is omitted.

The chromatic aberration of magnification of the objective optical system for an endoscope according to Example 5 will be described hereinafter. The maximum image height IH thereof is 0.664 mm. As illustrated in FIG. 6E, the chromatic aberration of magnification is 1.5 µm or less, and this corresponds to 0.23% of half side of the diagonal. In the same manner as the objective optical system for an endoscope according to Example 1, it is considered that the chromatic aberration of magnification causes no problem.

The total length of the objective optical system for an endoscope according to Example 5 will be described hereinafter. The distance from the first surface on the object side of the lens to the image surface is 5.05 times as long as the focal length, and shorter than the prior art documents. For this reason, it is suitable for an objective optical system used for an endoscope with a small-sized distal end portion and high image quality.

Example 6

Figure 7A:
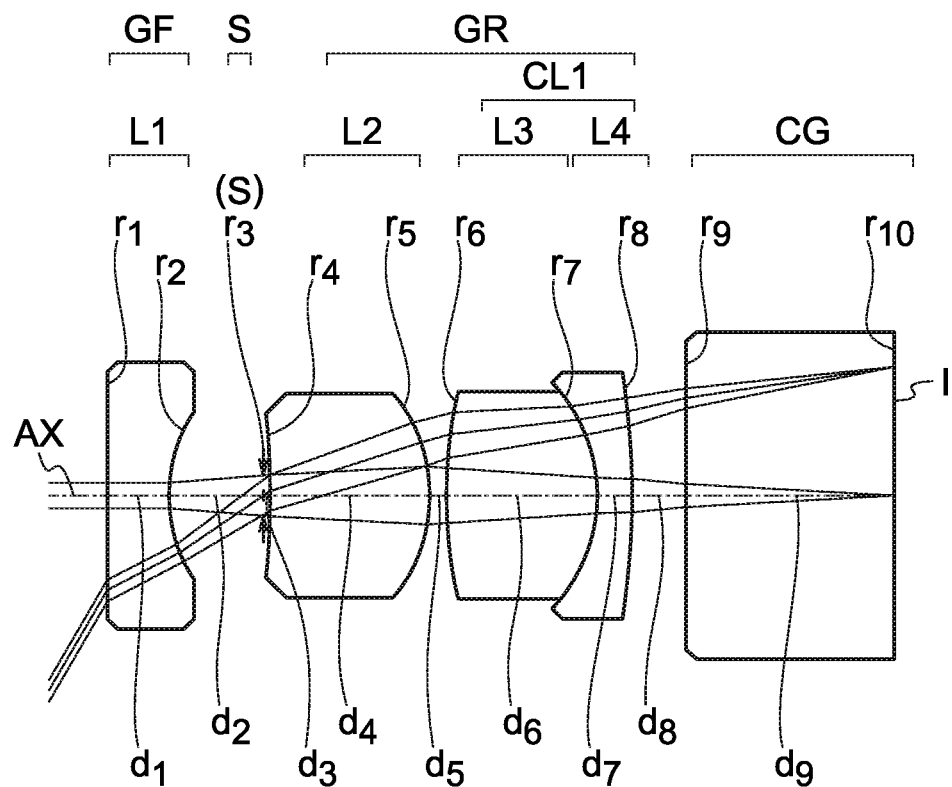
FIG. 7A is a lens cross-sectional view of an objective optical system for an endoscope according to Example 6.
Figures 7B, 7C, 7D, 7E:
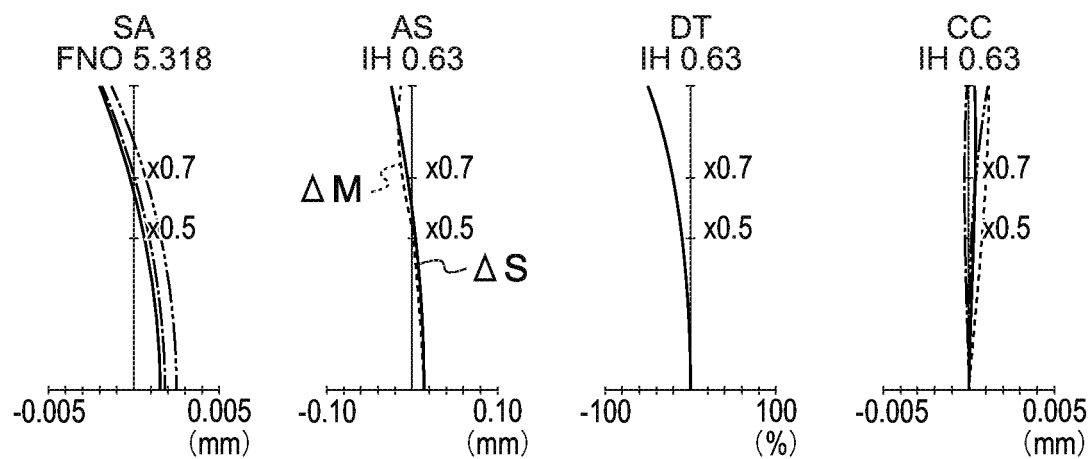
FIG. 7B, FIG. 7C, FIG. 7D, and FIG. 7E are aberration diagrams illustrating spherical aberration (SA), astigmatism (AS), distortion (DT), and chromatic aberration of magnification (CC) of the present example, respectively.

An objective optical system for an endoscope according to Example 6 will be described hereinafter. FIG. 7A is a lens cross-sectional view of the objective optical system for an endoscope according to Example 6. FIG. 7B illustrates spherical aberration (SA), FIG. 7C illustrates astigmatism (AS), FIG. 7D illustrates distortion (DT), and FIG. 7E illustrates chromatic aberration of magnification (CC).

The objective optical system for an endoscope according to Example 6 includes, in order from the object side, a front group GF having a negative refractive power, an aperture stop S, and a rear group GR having a positive refractive power, as illustrated in FIG. 7A.

In the objective optical system for an endoscope according to Example 6, a glass material of nd=1.883 is used for the negative first lens L1, a glass material of nd=1.816 is used for the positive second meniscus lens L2, and a glass material of nd=1.651 is used for the negative fourth meniscus lens L4 of the cemented lens CL1.

In Example 6, optical glass other than sapphire is used as the glass material of the negative first lens L1. Although mechanical durability of the optical glass is inferior to that of sapphire, workability of the optical glass is superior to that of sapphire. By virtue of advantage of the price and workability of the optical glass, it is possible to manufacture the lens at lower cost than that in the case of using sapphire.

The structure and the conditional expressions of the rear group GR in Example 6 are the same as the structure and the conditional expressions in Example 5, and an overlapping explanation is omitted.

The chromatic aberration of magnification of the objective optical system for an endoscope according to Example 6 will be described hereinafter. The maximum image height IH thereof is 0.625 mm. As illustrated in FIG. 7E, the chromatic aberration of magnification is 1.5 µm or less, and this corresponds to 0.24% of half side of the diagonal. In the same manner as the objective optical system for an endoscope according to Example 1, it is considered that the chromatic aberration of magnification causes no problem.

The total length of the objective optical system for an endoscope according to Example 6 will be described hereinafter. The distance from the first surface on the object side of the lens to the image surface is 5.38 times as long as the focal length, and shorter than the prior art documents. For this reason, it is suitable for an objective optical system used for an endoscope with a small-sized distal end portion and high image quality.

Numerical data of each of Examples described above will be described hereinafter.

As an explanation of symbols, r denotes a curvature radius of each surface, d denotes thickness or an air interval of each optical member, nd denotes a refractive index of each optical member with respect to d line, vd denotes an Abbe number of each optical member with respect to d line, IH denotes maximum image height, ndCLn denotes a refractive index of d line of the negative fourth meniscus lens L4 in the cemented lens CL1 of the rear group GR, ndL2 denotes a refractive index of d line of the positive second meniscus lens (single lens) L2 of the rear group GR, ΔvdCL denotes a difference between an Abbe number of the positive lens L3 and an Abbe number of the negative fourth meniscus lens L4 in the cemented lens CL1 of the rear group GR, ft denotes a focal length of the entire system of the objective optical system, fL2 denotes a focal length of the positive second meniscus lens (single lens) L2 of the rear group GR, R1L1 denotes a curvature radius of the image side surface of the negative first lens (single lens) L1 of the front group GF, R1 denotes a curvature radius of the object side surface of the positive second lens (single lens) L2 in the rear group GR, R2 denotes a curvature radius of the image side surface of the positive second lens (single lens) L2 in the rear group GR, R1CL denotes a curvature radius of the cemented surface of the cemented lens CL1 of the rear group GR, Ls2 denotes a distance along the optical axis AX from the aperture stop S to the image side surface of the positive second meniscus lens (single lens) L2, Lgf denotes a distance along the optical axis AX from the object side surface of the negative first lens (single lens) L1 of the front group GF to the aperture stop S, Lgr denotes a distance along the optical axis AX from the aperture stop S to a surface located most on the image side in the lenses of the rear group GR, D1 is a radius of a spherical (concave) segment of the image side surface of the negative first lens (single lens) L1 in the front group GF, in a direction perpendicular to the optical axis AX, FNO denotes an F number, and ω denotes a half angle of view.

The unit of r, d, IH, ft, fL2, R1L1, R1, R2, R1CL, Ls2, Lgf, Lgr, and D1 is "mm". The unit of ω is "°" (degree), and the stop is the aperture stop.

Example 1

Unit mm

Surface data

| Surface no. | r | d | nd | vd |
|---|---|---|---|---|
| 1 | ∞ | 0.28 | 1.76820 | 71.79 |
| 2 | 0.667 | 0.17 | 1 | — |
| 3 | ∞ | 0.40 | 1.52100 | 65.13 |
| 4 | ∞ | 0.02 | 1 | — |
| 5 (Stop) | ∞ | 0.03 | 1 | — |
| 6 | −3.320 | 0.71 | 1.81600 | 60.08 |
| 7 | −0.729 | 0.08 | 1 | — |
| 8 | 1.740 | 0.54 | 1.56883 | 50.80 |
| 9 | −0.874 | 0.23 | 1.95906 | 17.47 |
| 10 | −2.744 | 0.44 | 1 | — |
| 11 | ∞ | 0.98 | 1.51633 | 64.14 |
| 12 | Image pickup surface I ∞ | | | |

Various data

| | |
|---|---|
| IH | 0.652 |
| ft | 0.726 |
| Ls2 | 0.740 |
| Lgf | 0.870 |
| Lgr | 1.590 |
| D1 | 0.409 |
| FNO | 5.540 |
| 2ω | 121.9 |

Example 2

Unit mm

Surface data

| Surface no. | r | d | nd | vd |
|---|---|---|---|---|
| 1 | ∞ | 0.28 | 1.76820 | 71.79 |
| 2 | 0.667 | 0.17 | 1 | — |
| 3 | ∞ | 0.40 | 1.52100 | 65.13 |
| 4 | ∞ | 0.02 | 1 | — |
| 5 (Stop) | ∞ | 0.03 | 1 | — |
| 6 | −3.397 | 0.79 | 1.83480 | 42.73 |
| 7 | −0.746 | 0.08 | 1 | — |
| 8 | 1.783 | 0.50 | 1.58313 | 59.38 |
| 9 | −0.843 | 0.20 | 1.95906 | 17.47 |
| 10 | −2.744 | 0.43 | 1 | — |
| 11 | ∞ | 0.98 | 1.51633 | 64.14 |
| 12 | Image pickup surface I ∞ | | | |

Various data

| | |
|---|---|
| IH | 0.615 |
| ft | 0.686 |
| Ls2 | 0.818 |
| Lgf | 0.870 |
| Lgr | 1.603 |
| D1 | 0.409 |
| FNO | 5.233 |
| 2ω | 121.1 |

Example 3

Unit mm

Surface data

| Surface no. | r | d | nd | vd |
|---|---|---|---|---|
| 1 | ∞ | 0.28 | 1.76820 | 71.79 |
| 2 | 0.667 | 0.17 | 1 | — |
| 3 | ∞ | 0.40 | 1.52100 | 65.13 |
| 4 | ∞ | 0.02 | 1 | — |
| 5 (Stop) | ∞ | 0.03 | 1 | — |
| 6 | −3.142 | 0.73 | 1.77250 | 49.60 |
| 7 | −0.690 | 0.08 | 1 | — |
| 8 | 1.643 | 0.58 | 1.53775 | 74.70 |
| 9 | −0.943 | 0.21 | 1.95906 | 17.47 |
| 10 | −2.744 | 0.36 | 1 | — |
| 11 | ∞ | 0.98 | 1.51633 | 64.14 |
| 12 | Image pickup surface I ∞ | | | |

| Various data | |
|---|---|
| IH | 0.625 |
| ft | 0.699 |
| Ls2 | 0.763 |
| Lgf | 0.870 |
| Lgr | 1.633 |
| D1 | 0.409 |
| FNO | 5.330 |
| 2ω | 121.9 |

Example 4

Unit mm

| Surface data | | | | |
|---|---|---|---|---|
| Surface no. | r | d | nd | νd |
| 1 | ∞ | 0.30 | 1.88300 | 40.76 |
| 2 | 0.820 | 0.17 | 1 | — |
| 3 | ∞ | 0.44 | 1.52100 | 65.13 |
| 4 | ∞ | 0.02 | 1 | — |
| 5 (Stop) | ∞ | 0.03 | 1 | — |
| 6 | −4.433 | 0.78 | 1.81600 | 46.62 |
| 7 | −0.750 | 0.08 | 1 | — |
| 8 | 2.172 | 0.68 | 1.64000 | 60.08 |
| 9 | −0.823 | 0.20 | 1.95906 | 17.47 |
| 10 | −3.048 | 0.30 | 1 | — |
| 11 | ∞ | 0.98 | 1.51633 | 64.14 |
| 12 | Image pickup surface I ∞ | | | |

| Various data | |
|---|---|
| IH | 0.622 |
| ft | 0.699 |
| Ls2 | 0.810 |
| Lgf | 0.929 |
| Lgr | 1.773 |
| D1 | 0.473 |
| FNO | 5.312 |
| 2ω | 119.5 |

Example 5

Unit mm

| Surface data | | | | |
|---|---|---|---|---|
| Surface no. | r | d | nd | νd |
| 1 | ∞ | 0.28 | 1.76820 | 71.79 |
| 2 | 0.687 | 0.44 | 1 | — |
| 3 (Stop) | ∞ | 0.03 | 1 | — |
| 4 | −3.900 | 0.71 | 1.81600 | 46.62 |
| 5 | −0.734 | 0.03 | 1 | — |
| 6 | 2.500 | 0.63 | 1.62230 | 53.17 |
| 7 | −0.840 | 0.18 | 1.95906 | 17.47 |
| 8 | −2.545 | 0.45 | 1 | — |
| 9 | ∞ | 0.98 | 1.51633 | 64.14 |
| 10 | Image pickup surface I ∞ | | | |

| Various data | |
|---|---|
| IH | 0.664 |
| ft | 0.754 |
| Ls2 | 0.740 |
| Lgf | 0.722 |
| Lgr | 1.629 |
| D1 | 0.416 |
| FNO | 5.650 |
| 2ω | 121.2 |

Example 6

Unit mm

| Surface data | | | | |
|---|---|---|---|---|
| Surface no. | r | d | nd | νd |
| 1 | ∞ | 0.28 | 1.88300 | 40.76 |
| 2 | 0.820 | 0.46 | 1 | — |
| 3 (Stop) | ∞ | 0.03 | 1 | — |
| 4 | −4.600 | 0.78 | 1.81600 | 46.62 |
| 5 | −0.753 | 0.08 | 1 | — |
| 6 | 2.022 | 0.74 | 1.65100 | 56.16 |
| 7 | −0.790 | 0.17 | 1.95906 | 17.47 |
| 8 | −3.492 | 0.26 | 1 | — |
| 9 | ∞ | 0.98 | 1.51633 | 64.14 |
| 10 | Image pickup surface I ∞ | | | |

| Various data | |
|---|---|
| IH | 0.625 |
| ft | 0.711 |
| Ls2 | 0.810 |
| Lgf | 0.755 |
| Lgr | 1.795 |
| D1 | 0.473 |
| FNO | 5.318 |
| 2ω | 121.0 |

Values corresponding to the conditional expressions will be illustrated hereinafter.

TABLE 1

| Conditional expression | | Example 1 | Example 2 | Example 3 | Example 4 | Example 5 | Example 6 |
|---|---|---|---|---|---|---|---|
| (1) | ndCLn | 1.959 | 1.959 | 1.959 | 1.959 | 1.959 | 1.959 |
| (2) | Δ ν dCL | 38.89 | 41.91 | 57.23 | 42.61 | 35.70 | 38.69 |
| (3) | fL2/ft | 1.395 | 1.461 | 1.441 | 1.438 | 1.328 | 1.415 |
| (4) | ndL2 | 1.820 | 1.839 | 1.776 | 1.820 | 1.820 | 1.820 |
| (5) | R1/ft | −4.570 | −4.950 | −4.495 | −6.343 | −5.170 | −6.470 |
| (6) | |R2/Ls2| | 0.985 | 0.912 | 0.904 | 0.926 | 0.992 | 0.930 |

TABLE 1-continued

| | Conditional expression | Example 1 | Example 2 | Example 3 | Example 4 | Example 5 | Example 6 |
|---|---|---|---|---|---|---|---|
| (7) | Lgr/Lgf | 1.828 | 1.842 | 1.877 | 1.909 | — | — |
| (8) | Lgr/ft | 2.159 | 2.336 | 2.336 | 2.537 | 2.159 | 2.525 |
| (9) | D1/R1L1 | 0.613 | 0.613 | 0.613 | 0.577 | 0.605 | 0.577 |
| (10) | R1CL/ft | −1.203 | −1.229 | −1.350 | −1.178 | −1.114 | −1.111 |

Various embodiments of the present disclosure have been explained above, but the present disclosure is not limited only to these embodiments. Embodiments formed by properly combining the structures of these embodiments within a range not departing from the gist thereof also fall under the category of the present disclosure.

As described above, the present disclosure is useful for an objective optical system having a small diameter, a short total length of the optical system, and a wide angle of view, and favorably correcting various aberrations, such as chromatic aberration and curvature of field.

According to the present disclosure, it is possible to provide an objective optical system having a small diameter, a short total length of the optical system, and a wide angle of view, and favorably correcting various aberrations, such as chromatic aberration and curvature of field.

What is claimed is:

1. An objective optical system comprising:
in order from an object side to an image side, a front group having a negative refractive power;
an aperture stop; and
a rear group having a positive refractive power,
wherein,
the front group includes a negative single lens,
the rear group includes, in order from the object side, a positive single lens and one or more cemented lenses, and
conditional expressions (1), (2), (3), and (5) are satisfied:

$$1.95 < ndCLn \quad (1)$$

$$35 < \Delta vdCL \quad (2)$$

$$1.1 < fL2/ft < 1.6 \quad (3)$$

$$-7 < R1/ft < -3.6 \quad (5)$$

where:
ndCLn denotes a refractive index of d line (wavelength of 587.6 nm) of a negative lens in the cemented lens,
ΔvdCL denotes a difference between an Abbe number of a positive lens and an Abbe number of the negative lens in the cemented lens,
ft denotes a focal length of an entire system of the objective optical system,
fL2 denotes a focal length of the positive single lens of the rear group, and
R1 denotes a curvature radius of an object side surface of the positive single lens.

2. The objective optical system according to claim 1, wherein, conditional expression (4) is satisfied:

$$1.75 < ndL2 \quad (4)$$

where:
ndL2 denotes a refractive index of d line of the positive single lens.

3. The objective optical system according to claim 1, wherein, conditional expression (6) is satisfied:

$$0.8 < |R2/Ls2| 1.2 \quad (6)$$

where:
R2 denotes a curvature radius of an image side surface of the positive single lens, and
Ls2 denotes a distance along an optical axis from the aperture stop to the image side surface of the positive single lens.

4. The objective optical system according to claim 1, wherein,
the front group includes a parallel plate, and
following conditional expression (7) is satisfied:

$$1.4 < Lgr/Lgf < 2 \quad (7)$$

where:
Lgf denotes a distance along an optical axis from an object side surface of the negative single lens to the aperture stop, and
Lgr denotes a distance along the optical axis from the aperture stop to a surface located most on the image side in the lenses of the rear group.

5. The objective optical system according to claim 1, wherein,
the front group includes only the negative single lens, and conditional expression (8) is satisfied:

$$1.9 < Lgr/ft < 2.6 \quad (8)$$

where:
Lgr denotes a distance along an optical axis from the aperture stop to a surface located most on the image side in the lenses of the rear group, and
ft denotes the focal length of the entire system of the objective optical system.

6. The objective optical system according to claim 4, wherein,
the negative single lens is a plano-concave lens including a flat surface disposed as the object side surface and conditional expression (9) is satisfied:

$$0.5 < D1/R1L1 < 0.9 \quad (9)$$

where
R1L1 denotes a curvature radius of an image side surface of the negative single lens, and
D1 is a radius of a spherical segment of the image side surface of the negative single lens, in a direction perpendicular to the optical axis.

7. The objective optical system according to claim 4, wherein
the cemented lens is formed of, in order from the object side, the positive lens and the negative lens, and conditional expression (10) is satisfied:

$$-2 < R1CL/ft < -1.1 \quad (10)$$

where
R1CL denotes a curvature radius of a cemented surface of the cemented lens, and ft denotes the focal length of the entire system of the objective optical system.

8. An image pickup apparatus comprising:
the objective optical system according to claim 1; and
an image sensor.

9. The image pickup apparatus according to claim 8, wherein, in the objective system, conditional expression (4) is satisfied:

$$1.75 < ndL2 \qquad (4)$$

where:
ndL2 denotes a refractive index of d line of the positive single lens.

10. The image pickup apparatus according to claim 8, wherein, in the objective system, conditional expression (6) is satisfied:

$$0.8 < |R2/Ls2| 1.2 \qquad (6)$$

where:
R2 denotes a curvature radius of an image side surface of the positive single lens, and
Ls2 denotes a distance along an optical axis from the aperture stop to the image side surface of the positive single lens.

11. The image pickup apparatus according to claim 8, wherein, in the objective system, wherein, the front group includes a parallel plate, and
conditional expression (7) is satisfied:

$$1.4 < Lgr/Lgf < 2 \qquad (7)$$

where
Lgf denotes a distance along an optical axis from an object side surface of the negative single lens to the aperture stop, and
Lgr denotes a distance along the optical axis from the aperture stop to a surface located most on the image side in the lenses of the rear group.

12. The image pickup apparatus according to claim 8, wherein, in the objective optical system,
the front group includes only the negative single lens, and
conditional expression (8) is satisfied:

$$1.9 < Lgr/ft < 2.6 \qquad (8)$$

where:
Lgr denotes a distance along an optical axis from the aperture stop to a surface located most on the image side in the lenses of the rear group, and
ft denotes the focal length of the entire system of the objective optical system.

13. The image pickup apparatus according to claim 12, wherein,
the negative single lens is a plano-concave lens including a flat surface disposed as the object side surface and conditional expression (9) is satisfied:

$$0.5 < D1/R1L1 < 0.9 \qquad (9)$$

where
R1L1 denotes a curvature radius of an image side surface of the negative single lens, and
D1 is a radius of a spherical segment of the image side surface of the negative single lens, in a direction perpendicular to the optical axis.

14. An endoscope comprising:
the objective optical system according to claim 1; and
an image sensor.

15. The endoscope according to claim 14, wherein, in the objective system, conditional expression (4) is satisfied:

$$1.75 < ndL2 \qquad (4)$$

where:
ndL2 denotes a refractive index of d line of the positive single lens.

16. The endoscope according to claim 14, wherein, in the objective system, conditional expression (6) is satisfied:

$$0.8 < |R2/Ls2| 1.2 \qquad (6)$$

where:
R2 denotes a curvature radius of an image side surface of the positive single lens, and
Ls2 denotes a distance along an optical axis from the aperture stop to the image side surface of the positive single lens.

17. The endoscope according to claim 14, wherein, in the objective system,
the front group includes a parallel plate, and
following conditional expression (7) is satisfied:

$$1.4 < Lgr/Lgf < 2 \qquad (7)$$

where:
Lgf denotes a distance along an optical axis from an object side surface of the negative single lens to the aperture stop, and
Lgr denotes a distance along the optical axis from the aperture stop to a surface located most on the image side in the lenses of the rear group.

18. The endoscope comprising according to claim 14, wherein, in the objective system,
the front group includes only the negative single lens, and
following conditional expression (8) is satisfied:

$$1.9 < Lgr/ft < 2.6 \qquad (8)$$

where:
Lgr denotes a distance along an optical axis from the aperture stop to a surface located most on the image side in the lenses of the rear group, and
ft denotes the focal length of the entire system of the objective optical system.

19. The endoscope according to claim 17, wherein, in the objective system,
the negative single lens is a plano-concave lens including a flat surface disposed as the object side surface and conditional expression (9) is satisfied:

$$0.5 < D1/R1L1 < 0.9 \qquad (9)$$

where:
R1L1 denotes a curvature radius of an image side surface of the negative single lens, and
D1 is a radius of a spherical segment of the image side surface of the negative single lens, in a direction perpendicular to the optical axis.

20. The endoscope according to claim 17, wherein, in the objective system,
the cemented lens is formed of, in order from the object side, the positive lens and the negative lens, and
conditional expression (10) is satisfied:

$$-2 < R1CL/ft < -1.1 \qquad (10)$$

where
R1CL denotes a curvature radius of a cemented surface of the cemented lens, and
ft denotes the focal length of the entire system of the objective optical system.

* * * * *